(12) United States Patent
Sur et al.

(10) Patent No.: US 10,172,392 B2
(45) Date of Patent: Jan. 8, 2019

(54) HUMIDITY SENSING FOR AN AEROSOL DELIVERY DEVICE

(71) Applicant: RAI Strategic Holdings, Inc., Winston-Salem, NC (US)

(72) Inventors: Rajesh Sur, Winston-Salem, NC (US); Eric T. Hunt, Pfafftown, NC (US); Stephen B. Sears, Siler City, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 15/355,711

(22) Filed: Nov. 18, 2016

(65) Prior Publication Data

US 2018/0140008 A1 May 24, 2018

(51) Int. Cl.
| | | |
|---|---|---|
| A24F 47/00 | (2006.01) | |
| G01N 25/56 | (2006.01) | |
| G01N 27/04 | (2006.01) | |
| G01N 27/22 | (2006.01) | |
| H01G 11/08 | (2013.01) | |

(Continued)

(52) U.S. Cl.
CPC .......... *A24F 47/008* (2013.01); *G01N 25/56* (2013.01); *G01N 27/048* (2013.01); *G01N 27/223* (2013.01); *H01G 11/08* (2013.01); *H01M 10/0525* (2013.01); *H05B 1/0244* (2013.01); *H01M 2220/30* (2013.01)

(58) Field of Classification Search
CPC ... A24F 47/008; A61M 16/00; A61M 16/021; A61M 16/022; A61M 16/024; A61M 16/026
USPC .............................. 131/328, 329; 128/204.15
See application file for complete search history.

(56) References Cited

U.S. PATENT DOCUMENTS

| 1,771,366 A | 7/1930 | Wyss et al. |
|---|---|---|
| 2,057,353 A | 10/1936 | Whittemore, Jr. |

(Continued)

FOREIGN PATENT DOCUMENTS

| AU | 276250 | 7/1965 |
|---|---|---|
| CA | 2 641 869 | 5/2010 |

(Continued)

OTHER PUBLICATIONS

International Search Report for PCT/IB2017/057231, dated Jul. 3, 2018.

*Primary Examiner* — Tulsidas C Patel
*Assistant Examiner* — Peter G Leigh
(74) *Attorney, Agent, or Firm* — Womble Bond Dickinson (US) LLP

(57) ABSTRACT

An aerosol delivery device is provided. The aerosol delivery device comprises a control component and a humidity sensor. The humidity sensor is configured to measure a property thereof that is variable with relative humidity in an environment of the aerosol delivery device to which the humidity sensor is exposed. The humidity sensor is also configured to generate a corresponding signal that indicates a value of the property from which the relative humidity is calculable. The control component, or the humidity sensor, is configured to calculate the relative humidity from the value indicated by the corresponding signal, and control operation of at least one functional element of the aerosol delivery device based on the relative humidity so calculated, including output of the relative humidity for presentation by a display.

40 Claims, 3 Drawing Sheets

(51) Int. Cl.
*H01M 10/0525* (2010.01)
*H05B 1/02* (2006.01)

(56) References Cited

U.S. PATENT DOCUMENTS

| | | | |
|---|---|---|---|
| 2,104,266 A | 1/1938 | McCormick | |
| 3,200,819 A | 8/1965 | Gilbert | |
| 4,284,089 A | 8/1981 | Ray | |
| 4,303,083 A | 12/1981 | Burruss, Jr. | |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,965,698 A * | 10/1990 | Thoma | G01M 3/16 29/25.42 |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiling et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 * | 3/2011 | Hamano | A61M 11/041 128/204.15 |
| 8,127,772 B2 | 3/2012 | Montaser | |
| 8,314,591 B2 | 11/2012 | Terry et al. | |
| 8,365,742 B2 | 2/2013 | Hon | |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,851,081 B2 | 10/2014 | Fernando et al. | |
| 2002/0146242 A1 | 10/2002 | Vieira | |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2007/0227534 A1 * | 10/2007 | Nobutani | A61M 15/025 128/200.14 |
| 2007/0240706 A1 * | 10/2007 | Kobayashi | A61M 15/025 128/200.14 |
| 2007/0240711 A1 * | 10/2007 | Hamano | A61M 15/0095 128/203.12 |
| 2008/0011292 A1 * | 1/2008 | Sugita | A61M 5/16827 128/200.19 |
| 2008/0022998 A1 * | 1/2008 | Hamano | A61M 11/041 128/200.14 |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0050142 A1 * | 2/2009 | Hamano | A61M 15/02 128/200.23 |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 | 9/2010 | Hearn | |
| 2010/0242974 A1 | 9/2010 | Pan | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0309157 A1 | 12/2011 | Yang et al. | |
| 2012/0042885 A1 | 2/2012 | Stone et al. | |
| 2012/0060853 A1 | 3/2012 | Robinson et al. | |
| 2012/0111347 A1 | 5/2012 | Hon | |
| 2012/0132643 A1 | 5/2012 | Choi et al. | |
| 2012/0227752 A1 | 9/2012 | Alelov | |
| 2012/0231464 A1 | 9/2012 | Yu et al. | |
| 2012/0260927 A1 | 10/2012 | Liu | |
| 2012/0279512 A1 | 11/2012 | Hon | |
| 2012/0318882 A1 | 12/2012 | Abehasera | |
| 2013/0037041 A1 | 2/2013 | Worm et al. | |
| 2013/0056013 A1 | 3/2013 | Terry et al. | |
| 2013/0081625 A1 | 4/2013 | Rustad et al. | |
| 2013/0081642 A1 | 4/2013 | Safari | |
| 2013/0192619 A1 | 8/2013 | Tucker et al. | |

(56) References Cited

U.S. PATENT DOCUMENTS

| | | |
|---|---|---|
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2014/0345633 A1* | 11/2014 | Talon ............... A24F 47/008 131/329 |
| 2015/0007838 A1 | 1/2015 | Fernando et al. |
| 2015/0053217 A1 | 2/2015 | Steingraber et al. |
| 2015/0068541 A1* | 3/2015 | Sears ............... A24F 47/008 131/328 |
| 2015/0201674 A1* | 7/2015 | Dooly ............... A24F 47/008 53/432 |
| 2015/0230521 A1* | 8/2015 | Talon ............... A24F 47/008 131/328 |
| 2016/0037826 A1 | 2/2016 | Hearn et al. |
| 2016/0058074 A1* | 3/2016 | Liu ................. A24F 47/008 131/329 |
| 2016/0106152 A1* | 4/2016 | Liu ....................... G01F 1/661 392/404 |
| 2016/0185750 A1* | 6/2016 | Dull ..................... C07D 401/04 131/329 |
| 2016/0192713 A1* | 7/2016 | Memari ............... A24F 15/12 141/2 |
| 2016/0198767 A1* | 7/2016 | Verleur ............... H05B 1/0202 392/386 |
| 2016/0235124 A1* | 8/2016 | Krietzman ........... A24F 47/008 |
| 2016/0241146 A1* | 8/2016 | Oliaei ................. H02M 3/158 |
| 2016/0260318 A1* | 9/2016 | Zajac ................... G01D 21/02 |
| 2016/0331035 A1* | 11/2016 | Cameron ............... F01K 5/00 |
| 2016/0331037 A1* | 11/2016 | Cameron ............. A24F 47/008 |
| 2016/0334119 A1* | 11/2016 | Cameron ................. F24F 3/16 |
| 2016/0338407 A1* | 11/2016 | Kerdemelidis ....... A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 4 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 1 882 488 A2 | 1/2008 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

\* cited by examiner

HUMIDITY SENSING FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, it may be desirable to provide aerosol delivery devices with functionality for sensing the relative humidity within an environment of the aerosol delivery devices.

BRIEF SUMMARY

The present disclosure relates to aerosol delivery devices, methods of forming such devices, and elements of such devices. The present disclosure thus includes, without limitation, the following example implementations. In some example implementations, an aerosol delivery device is provided. The aerosol delivery device may include at least one housing enclosing a reservoir configured to retain an aerosol precursor composition, a heating element and a control component. The control component is configured to operate in an active mode in which the control component is configured to control the heating element to activate and vaporize components of the aerosol precursor composition. The humidity sensor is configured to measure a property thereof that is variable with relative humidity in an environment of the aerosol delivery device, and generate a corresponding signal that indicates a value of the property from which the relative humidity is calculable. The control component or the humidity sensor is further configured to calculate the relative humidity from the value indicated by the corresponding signal, and control operation of at least one functional element of the aerosol delivery device based on the relative humidity so calculated, including output of the relative humidity for presentation by a display.

In some example implementations of the aerosol device of the preceding or any subsequent example implementation, or any combination thereof, the humidity sensor is a capacitive, resistive or thermal conductive humidity sensor.

In some example implementations of the aerosol device of any preceding or any subsequent example implementation, or any combination thereof, the humidity sensor is a resistive humidity sensor, and the humidity sensor being configured to measure the property includes the resistive humidity sensor being configured to measure an impedance thereof that is exponentially proportional to the relative humidity in the environment.

In some example implementations of the aerosol device of any preceding or any subsequent example implementation, or any combination thereof, the humidity sensor is a capacitive humidity sensor, and the humidity sensor being configured to measure the property includes the capacitive humidity sensor being configured to measure a dielectric constant thereof that is directly proportional to the relative humidity in the environment.

In some example implementations of the aerosol device of any preceding or any subsequent example implementation, or any combination thereof, the aerosol delivery device further comprises a decoupling capacitor operatively coupled to the humidity sensor and configured to reduce noise associated with the corresponding signal.

In some example implementations of the aerosol device of any preceding or any subsequent example implementation, or any combination thereof, the aerosol delivery device further comprises a rechargeable power source configured to power the humidity sensor and including a lithium ion battery (LiB), thin-film solid state battery (SSB) or supercapacitor.

In some example implementations of the aerosol device of any preceding or any subsequent example implementation, or any combination thereof, the aerosol delivery device further comprises a linear regulator or a switching regulator operatively coupled between the power source and humidity sensor, and configured to direct a constant current from the power source to the humidity sensor.

In some example implementations of the aerosol device of any preceding or any subsequent example implementation, or any combination thereof, the humidity sensor is further configured to measure a temperature in the environment, and generate a second corresponding signal that indicates the temperature, and the control component or humidity sensor is further configured to control the at least one functional element includes being configured to control the at least one functional element further based on the temperature indicated by the second corresponding signal, and control of the at least one functional element additionally includes output of the temperature for presentation by the display.

In some example implementations of the aerosol device of any preceding or any subsequent example implementation, or any combination thereof, output of the relative humidity includes output of the relative humidity for presentation by the display in a tabular or graphic format.

In some example implementations of the aerosol device of any preceding or any subsequent example implementation, or any combination thereof, the aerosol delivery device further comprises a communication interface configured to enable wireless communication, and the control component or the humidity sensor is further configured to control operation of the at least one functional element includes being configured to cause the communication interface to wirelessly communicate the relative humidity to a computing device configured to control a humidification system in response thereto.

In some example implementations of the aerosol device of any preceding or any subsequent example implementation, or any combination thereof, the housing of the aerosol delivery device defines a mouthend having the humidity sensor positioned therein, and the environment of the aerosol delivery device includes a mouth of a user of the aerosol delivery device, and the control component or the humidity sensor being further configured to control operation of the at least one functional element of the aerosol delivery device based on the relative humidity so calculated includes being configured to alter a particle size of an aerosol produced thereby.

In some example implementations, a control body coupled or coupleable with a cartridge to form an aerosol delivery device is provided. The cartridge is equipped with a heating element and contains an aerosol precursor composition. The control body may include a housing, and within the housing, a control component and a humidity sensor. The control component is configured to operate in an active mode in which the control component is configured to control the heating element to activate and vaporize components of the aerosol precursor composition. The humidity sensor is configured to measure a property thereof that is variable with relative humidity in an environment of the aerosol delivery device, and generate a corresponding signal that indicates a value of the property from which the relative humidity is calculable. The control component or the humidity sensor is further configured to calculate the relative humidity from the value indicated by the corresponding signal, and control operation of at least one functional element of the aerosol delivery device based on the relative humidity so calculated, including output of the relative humidity for presentation by a display.

In some example implementations of the control body of the preceding or any subsequent example implementation, or any combination thereof, the humidity sensor is a capacitive, resistive or thermal conductive humidity sensor.

In some example implementations of the control body of any preceding or any subsequent example implementation, or any combination thereof, the humidity sensor is a resistive humidity sensor, and the humidity sensor being configured to measure the property includes the resistive humidity sensor being configured to measure an impedance thereof that is exponentially proportional to the relative humidity in the environment.

In some example implementations of the control body of any preceding or any subsequent example implementation, or any combination thereof, the humidity sensor is a capacitive humidity sensor, and the humidity sensor being configured to measure the property includes the capacitive humidity sensor being configured to measure a dielectric constant thereof that is directly proportional to the relative humidity in the environment.

In some example implementations of the control body of any preceding or any subsequent example implementation, or any combination thereof, the control body further comprises a decoupling capacitor operatively coupled to the humidity sensor and configured to reduce noise associated with the corresponding signal.

In some example implementations of the control body of any preceding or any subsequent example implementation, or any combination thereof, the control body further comprises a rechargeable power source configured to power the humidity sensor and including a lithium ion battery (LiB), thin-film solid state battery (SSB) or supercapacitor.

In some example implementations of the control body of any preceding or any subsequent example implementation, or any combination thereof, the control body further comprises a linear regulator or a switching regulator operatively coupled between the power source and humidity sensor, and configured to direct a constant current from the power source to the humidity sensor.

In some example implementations of the control body of any preceding or any subsequent example implementation, or any combination thereof, the humidity sensor is further configured to measure a temperature in the environment, and generate a second corresponding signal that indicates the temperature, and the control component or humidity sensor being further configured to control the at least one functional element includes being configured to control the at least one functional element further based on the temperature indicated by the second corresponding signal, and control of the at least one functional element additionally includes output of the temperature for presentation by the display.

In some example implementations of the control body of any preceding or any subsequent example implementation, or any combination thereof, output of the relative humidity includes output of the relative humidity for presentation by the display in a tabular or graphic format.

In some example implementations of the control body of any preceding or any subsequent example implementation, or any combination thereof, the control body further comprises a communication interface configured to enable wireless communication, and the control component or the humidity sensor being further configured to control operation of the at least one functional element includes being configured to cause the communication interface to wirelessly communicate the relative humidity to a computing device configured to control a humidification system in response thereto.

In some example implementations of the control body of any preceding or any subsequent example implementation, or any combination thereof, the housing of the aerosol delivery device defines a mouthend having the humidity sensor positioned therein, and the environment of the aerosol delivery device includes a mouth of a user of the aerosol delivery device, and the control component or the humidity sensor being further configured to control operation of the at least one functional element of the aerosol delivery device based on the relative humidity so calculated includes being configured to alter a particle size of an aerosol produced thereby.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
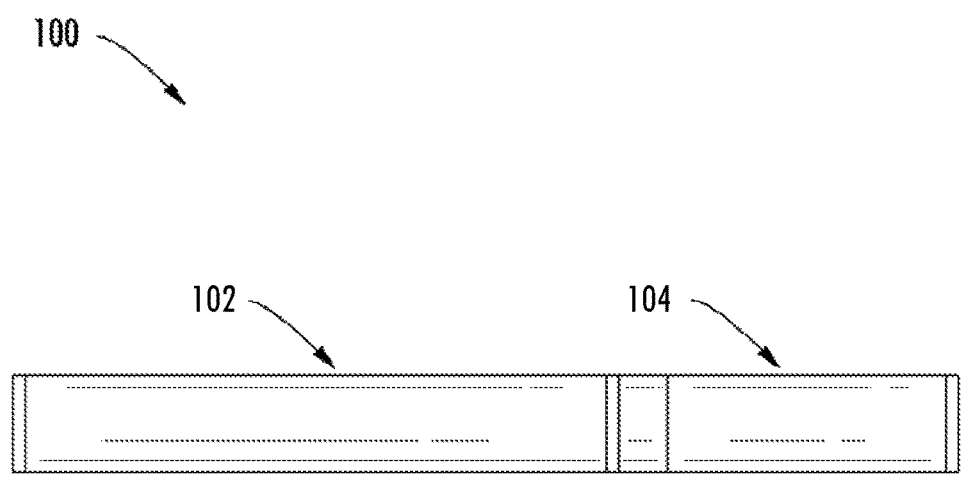
FIG. 1 illustrates a side view of an aerosol delivery device including a cartridge coupled to a control body, according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™, JET™, MAXXQ™, PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; AVIGO, VUSE, VUSE CONNECT, VUSE FOB, VUSE HYBRID, ALTO, ALTO+, MODO, CIRO, FOX+FOG, AND SOLO+ by R. J. Reynolds Vapor Company; MISTIC MENTHOL by Mistic Ecigs; and VYPE by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Additional manufacturers, designers, and/or assignees of components and related technologies that may be employed in the aerosol delivery device of the present disclosure include Shenzhen Jieshibo Technology of Shenzhen, China; Shenzhen First Union Technology of Shenzhen City, China; Safe Cig of Los Angeles, Calif.; Janty Asia Company of the Philippines; Joyetech Changzhou Electronics of Shenzhen, China; SIS Resources; B2B International Holdings of Dover, Del.; Evolv LLC of OH; Montrade of Bologna, Italy; Shenzhen Bauway Technology of Shenzhen, China; Global Vapor Trademarks Inc. of Pompano Beach, Fla.; Vapor Corp. of Fort Lauderdale, Fla.; Nemtra GMBH of Raschau-Markersbach, Germany; Perrigo L. Co. of Allegan, Mich.; Needs Co., Ltd.; Smokefree Innotec of Las Vegas, Nev.; McNeil AB of Helsingborg, Sweden; Chong Corp; Alexza Pharmaceuticals of Mountain View, Calif.; BLEC, LLC of Charlotte, N.C.; Gaitrend Sarl of Rohrbach-les-Bitche, France; FeelLife Bioscience International of Shenzhen, China; Vishay Electronic BMGH of Selb, Germany; Shenzhen Smaco Technology Ltd. of Shenzhen, China; Vapor Systems International of Boca Raton, Fla.; Exonoid Medical Devices of Israel; Shenzhen Nowotech Electronic of Shenzhen, China; Minilogic Device Corporation of Hong Kong, China; Shenzhen Kontle Electronics of Shenzhen, China, and Fuma International, LLC of Medina, Ohio, 21st Century Smoke of Beloit, Wis., and Kimree Holdings (HK) Co. Limited of Hong Kong, China.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery (e.g., a rechargeable lithium ion battery) and thus may be combined with any type of recharging technology, including connection to a typical wall outlet, connection to a car charger (i.e., a cigarette lighter receptacle), connection to a computer, such as through a universal serial bus (USB) cable or connector, connection to a photovoltaic cell (sometimes referred to as a solar cell) or solar panel of solar cells (e.g., gallium arsenide (GaAs) solar cell with an efficiency of 28%), or connection to a RF-to-DC converter. Further, in some example implementations, the cartridge may comprise a single-use cartridge, as disclosed in U.S. Pat. No. 8,910,639 to Chang et al., which is incorporated herein by reference.

Figure 2:
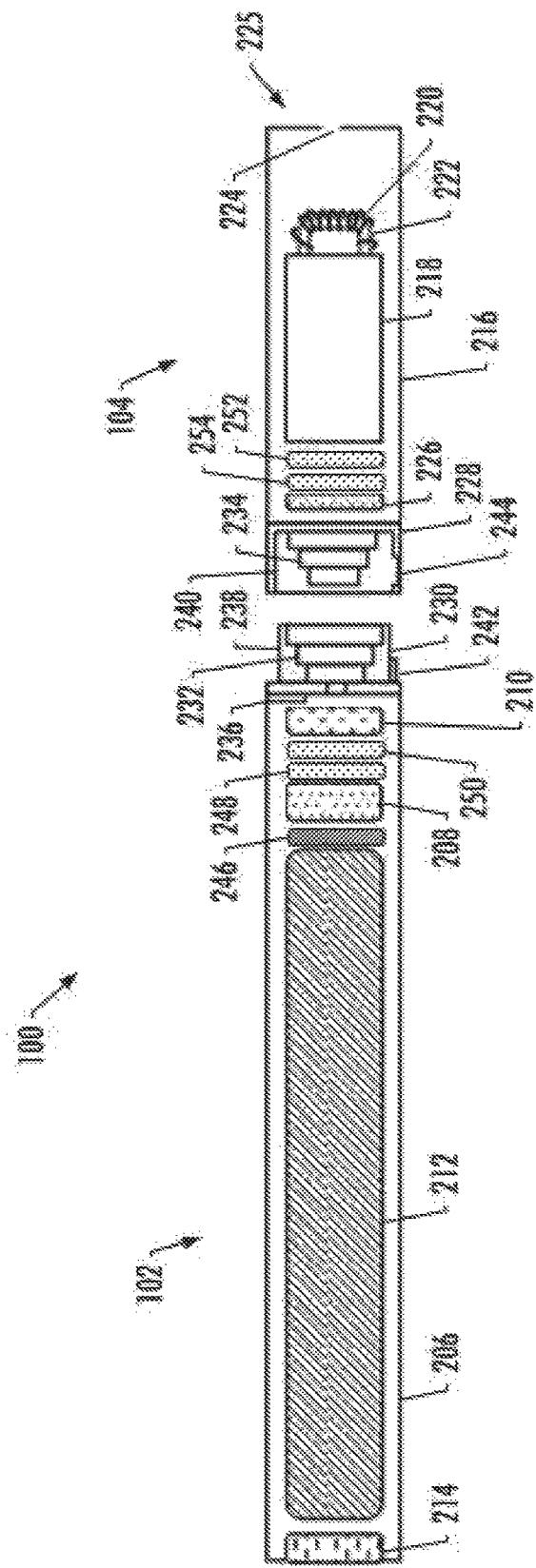
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, and such components can be variably aligned. The LED may be one example of a suitable visual indicator with which the aerosol delivery device may be equipped. Other indicators such as audio indicators (e.g., speakers), haptic indicators (e.g., vibration motors) or the like can be included in addition to or as an alternative to visual indicators such as the LED.

The power source 212 may include, for example, a battery (single-use or rechargeable) such as a single-use or rechargeable lithium-ion battery (LiB), solid-state battery (SSB), thin-film SSB, supercapacitor or the like, or some combination thereof. Some examples of a suitable power source are provided in U.S. patent application Ser. No. 14/918,926 to Sur et al., filed Oct. 21, 2015, which is incorporated herein by reference.

Examples of suitable solid-state batteries are STMicroelectronics' EnFilm™ rechargeable solid-state lithium thin-film batteries, which feature a $LiCoO_2$ cathode, LiPON ceramic electrolyte and a lithium anode. In particular, the EFL700A39 battery from STMicroelectronics has a nominal voltage of 4.1V and thickness of only 220 um. The battery is rated for a 10-year life time, and a 4000 charge-discharge cycle life. The battery also has a relatively short typical charge, in some instances charging in approximately 30 minutes (e.g., up to 30 minutes before the battery is fully (100%) charged or up to 10 minutes before the battery is at least 80% charged). The battery has a ceramic electrolyte, which may produce currents by movements of electrons and thus reduce the risk of undesirable dendrite growth in the cathode and anode that may otherwise lead to a short circuit. The ceramic electrolyte may also prevent a fire hazard upon contact with fire. In some examples, the solid electrolyte may avoid the solid electrolyte interface (SEI).

The supercapacitor may be any of a number of different types of supercapacitors, such as an electric double-layer capacitor (EDLC), a hybrid capacitor such as a lithium-ion capacitor (LIC), or the like. Supercapacitors such as EDLCs may be rated for a fast charge (e.g., three seconds). The supercapacitor be rated for a long lifetime (e.g., 32 years) and cycle life (e.g., 1,000,000 charge-discharge cycles), and provide an environmentally-friendly, lower-cost solution. The supercapacitor may provide high-current pulses to the electrical load. And as the supercapacitor does not include an inflammable electrolyte between the electrodes, the supercapacitor may therefore operate with only a negligible probability of a short circuit.

Hybrid capacitors such as the LIC generally have features of a battery (high voltage and high energy density), while maintaining the traditional characteristics of a capacitor of rapid charge (e.g., three (3) to one-hundred twenty (120) seconds). A hybrid capacitor may be rechargeable, and have the ability to operate on its own for a longer period without the need of another source of energy from which the hybrid capacitor may be chargeable. The hybrid capacitor may have a longer lifetime (e.g., 10 years) and cycle life as compared to other options, and is more environmentally friendly.

The cartridge 104 can be formed of a cartridge shell 216 enclosing a reservoir 218 configured to retain the aerosol precursor composition, and including a heater 220 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

As shown, in some examples, the reservoir 218 may be in fluid communication with a liquid transport element 222 adapted to wick or otherwise transport an aerosol precursor composition stored in the reservoir housing to the heater 220. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 220. The heater in these examples may be a resistive heating element such as a wire coil, micro heater or the like. Example materials from which the heating element may be formed include Kanthal (FeCrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend 225) to allow for egress of formed aerosol from the cartridge 104.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on an electronic printed circuit board (PCB) that supports and electrically connects the electronic components. Further, the PCB may be positioned horizontally relative the illustration of FIG. 1 in that the PCB can be lengthwise parallel to the central axis of the control body. In some examples, the air flow sensor may comprise its own PCB or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate. In some examples, a double sided PCB may be used to enable a substantially smaller form factor.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 220 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action to the heater 220 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 220 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, under voltage lockout protection, over voltage protection, over temperature protection, electrolyte compensation and charging input. The power-source protection circuit may include short-circuit protection, under-voltage lock out and/or over-voltage charge protection. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may also include a proximity sensor configured to measure a fluid level of the e-liquid in real-time, as described in U.S. patent application Ser. No. 15/261,307 to Sur et al., filed Sep. 9, 2016, which is incorporated herein by reference. The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference.

The aerosol delivery device 100 can incorporate the sensor 210 or another sensor or detector for control of supply of electric power to the heater 220 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

The aerosol delivery device 100 most preferably incorporates the control component 208 or another control mechanism for controlling the amount of electric power to the heater 220 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. Pat. App. Pub. No. 2015/0257445 to Henry et al., all of which are incorporated herein by reference.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. App. Pub. No. 2014/0209105 to Sears et al., which is incorporated herein by reference.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., and U.S. patent application Ser. No. 15/222,615 to Watson et al., filed Jul. 28, 2016, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. App. Pub. No. 2015/0216233 to Sears et al., all of which are incorporated herein by reference. The LED components may also have quantum dots embedded therein for higher efficiency.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference.

As indicated above, the control component 208 includes a number of electronic components, and in some examples may be formed of a PCB. The electronic components may include a microprocessor or processor core, and a memory. In some examples, the control component may include a microcontroller with integrated processor core and memory which may be an electrically erasable programmable read-only memory (EEPROM) or flash memory, and may further include one or more integrated input/output peripherals. In some examples, the control component may be coupled to a communication interface 246 to enable wireless communication (e.g., wireless communication via a Bluetooth low energy (BLE) device or WiFi) with one or more networks, computing devices or other appropriately-enabled devices.

Examples of suitable communication interfaces are disclosed in U.S. patent application Ser. No. 14/638,562 to Marion et al., filed Mar. 4, 2015, the content of which is incorporated herein by reference. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

In accordance with some example implementations, the control body 102 may include a humidity sensor 248 configured to measure a property thereof that is variable with relative humidity in an environment of the aerosol delivery device (to which the humidity sensor is exposed). The humidity sensor may then generate a corresponding signal that indicates a value of the property from which the relative humidity is calculable.

Examples of a suitable humidity sensor 248 may be or include a capacitive, resistive or thermal conductive humidity sensor. In some examples, the humidity sensor may generate a digital output which may be presented on a display (e.g., an LED panel) or transmitted via wireless communication (e.g., using a BLE device) to a remote device or application. For instance, the humidity sensor may be a capacitive humidity sensor configured to measure the property including measuring a dielectric constant thereof that is directly proportional to the relative humidity in the environment. In another instance, the humidity sensor may be a resistive humidity sensor configured to measure the property including measuring an impedance thereof that is exponentially proportional to the relative humidity in the environment. In some examples, the humidity sensor may be positioned within the mouthend of the aerosol delivery device to enable measurement of the humidity inside the mouth of the user. In these examples, based on the measured humidity inside the mouth of the user, the aerosol delivery device may produce aerosol of a certain particle size that correlates to a user-specific humidity profile for an optimal puff.

Examples of suitable capacitive humidity sensors are disclosed in U.S. Pat. No. 6,647,782 to Toyoda and U.S. Pat. No. 7,032,448 to Hamamoto, each of which is incorporated herein by reference. Examples of suitable resistive humidity sensors are disclosed in U.S. Pat. No. 6,229,318 to Suda, which is incorporated herein by reference. Examples of suitable thermal conductivity humidity sensors are disclosed in U.S. Pat. No. 6,843,100 to Blair, III et al., and U.S. Pat. App. Pub. No. 2015/0061706 to Kotnala et al., each of which is incorporated herein by reference.

Figure 3:
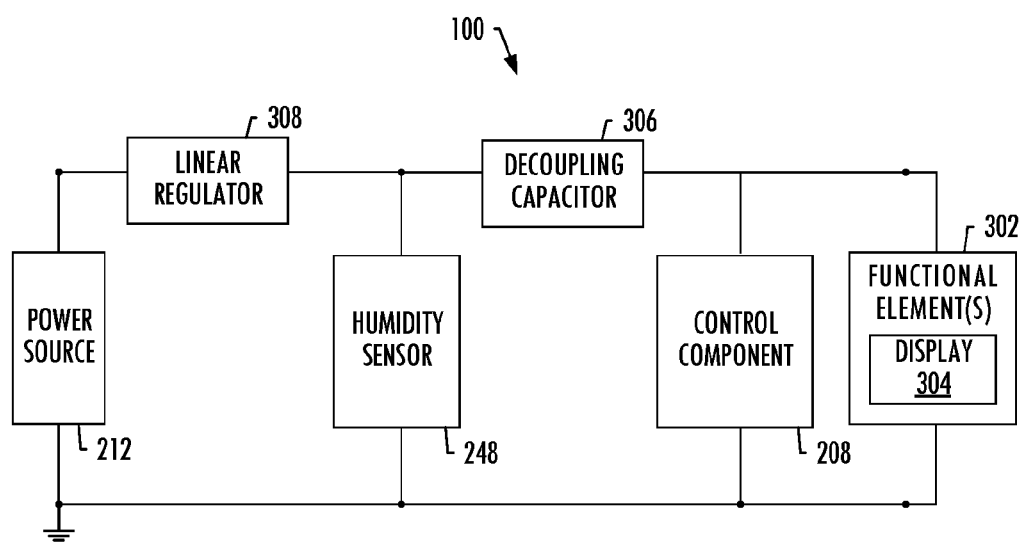
FIG. 3 illustrates various components of the aerosol delivery device of FIGS. 1 and 2, according to various example implementations.

FIG. 3 more particularly illustrates the aerosol delivery device 100 including the humidity sensor 248. As previously indicated, the humidity sensor may be configured to generate a corresponding signal that indicates a value of the property (measurable property of the humidity sensor) from which the relative humidity is calculable. The control component 208 or the humidity sensor may be configured to calculate the relative humidity from the value indicated by the corresponding signal, and control operation of at least one functional element 302 of the aerosol delivery device 100 based on the relative humidity so calculated.

Generally, the functional elements 302 of the aerosol delivery device 100 may be controlled in any of a number of different manners in response to the calculated relative humidity or measured temperature. For example, control of the functional element(s) 302 may include output of the relative humidity for presentation by a display 304. In another example, an indicator 250 (e.g., visual indicator, audio indicator, haptic indicator) may be controlled to provide a user-perceptible feedback (e.g., visual, audible, vibrational, haptic feedback). As yet another example, functional element(s) may be controlled to alter a locked state of the aerosol delivery device 100. This may include, for example, disabling one or more components of the aerosol delivery device from operation based on the calculated humidity.

In some examples, the humidity sensor 248 is also configured to measure a temperature in the environment, and generate a second corresponding signal that indicates the temperature. In these examples, the control component 208 or humidity sensor may be configured to control the functional element(s) 302 based on the temperature indicated by the second corresponding signal. Further, in these examples, the control component may be configured to control of the functional element(s) may additionally include output of the temperature for presentation by the display. In some examples, the relative humidity and temperature may be output for presentation by the display in a tabular or graphic format including a numerical value being presented on an LED display, for example.

In some examples in which the control body 102 includes a communication interface 246, control of the functional element(s) 302 may include control of the communication interface to cause the communication interface to wirelessly communicate (e.g., wireless communication via a Bluetooth low energy (BLE) device or WiFi) the relative humidity to a computing device external to the aerosol delivery device 100 (an external computing device). This computing device may also be embodied as a number of different devices configured to control a humidification system in response to the relative humidity being below a predetermined threshold. Examples of suitable computing devices include any of a number of different mobile computers, such as portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like.

As also shown in FIG. 3, the aerosol delivery device 100, and more specifically the control body 102 may include a number of electronic components, which may include a decoupling capacitor 306, linear regulator 308, switching regulator or the like. The decoupling capacitor may be operatively coupled to the humidity sensor 248 and configured to reduce noise associated with the corresponding signal. The rechargeable power source may be configured to power the humidity sensor, and may include a LiB, thin-film SSB or supercapacitor. In these examples, the linear regulator or switching regulator may be operatively coupled between the power source and humidity sensor, and configured to direct a constant current from the power source to the humidity sensor. In some alternative examples, the power source may be or include an energy harvesting device configured to boosts the voltage from a PV cell from 0.8 V to 3.5V and thereby provide the required power to the circuitry containing the humidity sensor without the need of a battery. Examples of suitable energy harvesting devices may include the Ultralow Power Energy Harvesting PMU with MPPT, Charge Management and Input Power Monitor (ADP5091) commercial product manufactured by Analog device.

Referring again to FIG. 2, in addition to or in lieu of the control body 102, the cartridge may include a humidity sensor 252 (e.g., capacitive, resistive or thermal conductivity humidity sensor), and perhaps also an indicator 254. Similar to above, functional element(s) of the aerosol delivery device 100 may be controlled in any of a number of different manners in response to the calculated relative humidity. For example, the relative humidity may be output for presentation by a display (e.g., LED display), or an indicator 250, 254 may be controlled to provide a user-perceptible feedback.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
    at least one housing enclosing a reservoir configured to retain an aerosol precursor composition;
    a heating element;
    a control component configured to operate in an active mode in which the control component is configured to control the heating element to activate and vaporize components of the aerosol precursor composition; and
    at least one sensor configured to measure a property of the at least one sensor that is variable with relative humidity in an environment of the aerosol delivery device, and generate a corresponding signal that indicates a value of the property from which the relative humidity is calculable, wherein the housing of the aerosol delivery device defines a mouthend having the at least one sensor positioned therein, and the environment of the aerosol delivery device includes a mouth of a user of the aerosol delivery device,
    wherein the control component or the at least one sensor is further configured to calculate the relative humidity from the value indicated by the corresponding signal, and control operation of at least one functional element of the aerosol delivery device based on the relative humidity so calculated, including being configured to alter a particle size of an aerosol produced thereby.

2. The aerosol delivery device of claim 1, wherein the at least one sensor is a capacitive, resistive or thermal conductive humidity sensor.

3. The aerosol delivery device of claim 1, wherein the at least one sensor is a resistive humidity sensor, and the at least one sensor being configured to measure the property includes the resistive humidity sensor being configured to measure an impedance thereof that is exponentially proportional to the relative humidity in the environment.

4. The aerosol delivery device of claim 1, wherein the at least one sensor is a capacitive humidity sensor, and the at least one sensor being configured to measure the property includes the capacitive humidity sensor being configured to measure a dielectric constant thereof that is directly proportional to the relative humidity in the environment.

5. The aerosol delivery device of claim 1 further comprising a decoupling capacitor operatively coupled to the at least one sensor and configured to reduce noise associated with the corresponding signal.

6. The aerosol delivery device of claim 1 further comprising a power source configured to power the at least one sensor and including a lithium ion battery (LiB), thin-film solid state battery (SSB) or supercapacitor.

7. The aerosol delivery device of claim 6 further comprising a linear regulator operatively coupled between the power source and at least one sensor, and configured to direct a constant current from the power source to the at least one sensor.

8. The aerosol delivery device of claim 1, wherein the control component or the at least one sensor being further configured to control operation of the at least one functional element of the aerosol delivery device includes output of the relative humidity for presentation by a display in a tabular or graphic format.

9. The aerosol delivery device of claim 1 further comprising a communication interface configured to enable wireless communication,
    wherein the control component or the at least one sensor being further configured to control operation of the at least one functional element includes being configured to cause the communication interface to wirelessly communicate the relative humidity to a computing device configured to control a humidification system in response thereto.

10. The aerosol delivery device of claim 1, wherein the at least one sensor is further configured to measure a temperature in the environment, and generate a second corresponding signal that indicates the temperature, and
    wherein the control component or the at least one sensor being further configured to control the at least one functional element includes being configured to control the at least one functional element further based on the temperature indicated by the second corresponding signal, and control of the at least one functional element additionally includes output of the temperature for presentation by a display.

11. A control body coupled or coupleable with a cartridge to form an aerosol delivery device, the cartridge being equipped with a heating element and containing an aerosol precursor composition, the control body comprising:
    a housing; and within the housing,
    a control component configured to operate in an active mode in which the control component is configured to control the heating element to activate and vaporize components of the aerosol precursor composition; and
    at least one sensor configured to measure a property of the at least one sensor that is variable with relative humidity in an environment of the aerosol delivery device, and generate a corresponding signal that indicates a value of the property from which the relative humidity is calculable, wherein the housing of the aerosol delivery device defines a mouthend having the at least one sensor positioned therein, and the environment of the aerosol delivery device includes a mouth of a user of the aerosol delivery device, wherein the control component or the at least one sensor is further configured to calculate the relative humidity from the value indicated by the corresponding signal, and control operation of at least one functional element of the aerosol delivery device based on the relative humidity so calculated, including being configured to alter a particle size of an aerosol produced thereby.

12. The control body of claim 11, wherein the at least one sensor is a capacitive, resistive or thermal conductive humidity sensor.

13. The control body of claim 11, wherein the at least one sensor is a resistive humidity sensor, and the at least one sensor being configured to measure the property includes the resistive humidity sensor being configured to measure an impedance thereof that is exponentially proportional to the relative humidity in the environment.

14. The control body of claim 11, wherein the at least one sensor is a capacitive humidity sensor, and the at least one sensor being configured to measure the property includes the capacitive humidity sensor being configured to measure a dielectric constant thereof that is directly proportional to the relative humidity in the environment.

15. The control body of claim 11 further comprising a decoupling capacitor operatively coupled to the at least one sensor and configured to reduce noise associated with the corresponding signal.

16. The control body of claim 11 further comprising a power source configured to power the at least one sensor and including a lithium ion battery (LiB), thin-film solid state battery (SSB) or supercapacitor.

17. The control body of claim 16 further comprising a linear regulator operatively coupled between the power source and at least one sensor, and configured to direct a constant current from the power source to the at least one sensor.

18. The control body of claim 11, wherein the control component or the at least one sensor being further configured to control operation of the at least one functional element of the aerosol delivery device includes output of the relative humidity for presentation by a display in a tabular or graphic format.

19. The control body of claim 11 further comprising a communication interface configured to enable wireless communication, wherein the control component or the at least one sensor being further configured to control operation of the at least one functional element includes being configured to cause the communication interface to wirelessly communicate the relative humidity to a computing device configured to control a humidification system in response thereto.

20. The control body of claim 11, wherein the at least one sensor is further configured to measure a temperature in the environment, and generate a second corresponding signal that indicates the temperature, and wherein the control component or the at least one sensor being further configured to control the at least one functional element includes being configured to control the at least one functional element further based on the temperature indicated by the second corresponding signal, and control of the at least one functional element additionally includes output of the temperature for presentation by a display.

21. An aerosol delivery device comprising:
at least one housing enclosing a reservoir configured to retain an aerosol precursor composition;
a heating element;
a control component configured to operate in an active mode in which the control component is configured to control the heating element to activate and vaporize components of the aerosol precursor composition; and
at least one sensor configured to measure a property of the at least one sensor that is variable with relative humidity in an environment of the aerosol delivery device, and generate a corresponding signal that indicates a value of the property from which the relative humidity is calculable, wherein the control component or the at least one sensor is further configured to calculate the relative humidity from the value indicated by the corresponding signal, and control operation of at least one functional element of the aerosol delivery device based on the relative humidity so calculated, wherein the control component or the at least one sensor being further configured to control operation of the at least one functional element of the aerosol delivery device includes being configured to alter a locked state of the aerosol delivery device by disabling one or more components of the aerosol delivery device from operation based on the calculated relative humidity.

22. The aerosol delivery device of claim 21, wherein the at least one sensor is a capacitive, resistive or thermal conductive humidity sensor.

23. The aerosol delivery device of claim 21, wherein the at least one sensor is a resistive humidity sensor, and the at least one sensor being configured to measure the property includes the resistive humidity sensor being configured to measure an impedance thereof that is exponentially proportional to the relative humidity in the environment.

24. The aerosol delivery device of claim 21, wherein the at least one sensor is a capacitive humidity sensor, and the at least one sensor being configured to measure the property includes the capacitive humidity sensor being configured to measure a dielectric constant thereof that is directly proportional to the relative humidity in the environment.

25. The aerosol delivery device of claim 21 further comprising a decoupling capacitor operatively coupled to the at least one sensor and configured to reduce noise associated with the corresponding signal.

26. The aerosol delivery device of claim 21 further comprising a power source configured to power the at least one sensor and including a lithium ion battery (LiB), thin-film solid state battery (SSB) or supercapacitor.

27. The aerosol delivery device of claim 26 further comprising a linear regulator operatively coupled between the power source and at least one sensor, and configured to direct a constant current from the power source to the at least one sensor.

28. The aerosol delivery device of claim 21, wherein the control component or the at least one sensor being further configured to control operation of the at least one functional element of the aerosol delivery device includes output of the relative humidity for presentation by a display in a tabular or graphic format.

29. The aerosol delivery device of claim 21 further comprising a communication interface configured to enable wireless communication, wherein the control component or the at least one sensor being further configured to control operation of the at least one functional element includes being configured to cause the communication interface to wirelessly communicate the relative humidity to a computing device configured to control a humidification system in response thereto.

30. The aerosol delivery device of claim 21, wherein the at least one sensor is further configured to measure a temperature in the environment, and generate a second corresponding signal that indicates the temperature, and
wherein the control component or the at least one sensor being further configured to control the at least one functional element includes being configured to control the at least one functional element further based on the temperature indicated by the second corresponding signal, and control of the at least one functional element additionally includes output of the temperature for presentation by a display.

31. A control body coupled or coupleable with a cartridge to form an aerosol delivery device, the cartridge being equipped with a heating element and containing an aerosol precursor composition, the control body comprising:
a housing; and within the housing,
a control component configured to operate in an active mode in which the control component is configured to control the heating element to activate and vaporize components of the aerosol precursor composition, and
at least one sensor configured to measure a property of the at least one sensor that is variable with relative humidity in an environment of the aerosol delivery device, and generate a corresponding signal that indicates a value of the property from which the relative humidity is calculable,
wherein the control component or the at least one sensor is further configured to calculate the relative humidity from the value indicated by the corresponding signal, and control operation of at least one functional element of the aerosol delivery device based on the relative humidity so calculated, wherein the control component or the at least one sensor being further configured to control operation of the at least one functional element of the aerosol delivery device includes being configured to alter a locked state of the aerosol delivery device by disabling one or more components of the aerosol delivery device from operation based on the calculated relative humidity.

32. The control body of claim 31, wherein the at least one sensor is a capacitive, resistive or thermal conductive humidity sensor.

33. The control body of claim 31, wherein the at least one sensor is a resistive humidity sensor, and the at least one sensor being configured to measure the property includes the resistive humidity sensor being configured to measure an impedance thereof that is exponentially proportional to the relative humidity in the environment.

34. The control body of claim 31, wherein the at least one sensor is a capacitive humidity sensor, and the at least one sensor being configured to measure the property includes the capacitive humidity sensor being configured to measure a dielectric constant thereof that is directly proportional to the relative humidity in the environment.

35. The control body of claim 31 further comprising a decoupling capacitor operatively coupled to the at least one sensor and configured to reduce noise associated with the corresponding signal.

36. The control body of claim 31 further comprising a power source configured to power the at least one sensor and including a lithium ion battery (LiB), thin-film solid state battery (SSB) or supercapacitor.

37. The control body of claim 36 further comprising a linear regulator operatively coupled between the power source and at least one sensor, and configured to direct a constant current from the power source to the at least one sensor.

38. The control body of claim 31, wherein the control component or the at least one sensor being further configured to control operation of the at least one functional element of the aerosol delivery device includes output of the relative humidity for presentation by a display in a tabular or graphic format.

39. The control body of claim 31 further comprising a communication interface configured to enable wireless communication,
wherein the control component or the at least one sensor being further configured to control operation of the at least one functional element includes being configured to cause the communication interface to wirelessly communicate the relative humidity to a computing device configured to control a humidification system in response thereto.

40. The control body of claim 31, wherein the at least one sensor is further configured to measure a temperature in the environment, and generate a second corresponding signal that indicates the temperature, and
wherein the control component or the at least one sensor being further configured to control the at least one functional element includes being configured to control the at least one functional element further based on the temperature indicated by the second corresponding signal, and control of the at least one functional element additionally includes output of the temperature for presentation by a display.

* * * * *